US012625127B2

(12) United States Patent
Miller et al.

(10) Patent No.: US 12,625,127 B2
(45) Date of Patent: May 12, 2026

(54) FIELD TEST FOR DETERMINING CONCENTRATION OF EMULSIFIERS IN DRILLING FLUIDS USING DYES

(71) Applicant: Halliburton Energy Services, Inc., Houston, TX (US)

(72) Inventors: Jeffrey J Miller, Houston, TX (US); Jay Deville, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 551 days.

(21) Appl. No.: 18/193,706

(22) Filed: Mar. 31, 2023

(65) Prior Publication Data

US 2024/0329029 A1 Oct. 3, 2024

(51) Int. Cl.
*G01N 1/38* (2006.01)
*G01N 33/28* (2006.01)

(52) U.S. Cl.
CPC ........... *G01N 33/2823* (2013.01); *G01N 1/38* (2013.01); *G01N 2001/388* (2013.01)

(58) Field of Classification Search
CPC ................. G01N 33/2823; G01N 1/38; G01N 2001/388; C09K 8/04
See application file for complete search history.

(56) References Cited

U.S. PATENT DOCUMENTS

| | | | |
|---|---|---|---|
| 6,925,392 | B2 | 8/2005 | McNeil, III et al. |
| 9,427,737 | B2 | 8/2016 | Heredia et al. |
| 11,473,426 | B2 | 10/2022 | Jamison et al. |

FOREIGN PATENT DOCUMENTS

| | | | |
|---|---|---|---|
| CN | 103940770 | B | 6/2016 |
| CN | 113848262 | A | 12/2021 |
| WO | 2021198770 | A1 | 7/2021 |

OTHER PUBLICATIONS

OFITE (“Methylene Blue Test Kit”). (Year: 2017).*

* cited by examiner

*Primary Examiner* — Charles Capozzi
*Assistant Examiner* — Michael Stanley Gzybowski
(74) *Attorney, Agent, or Firm* — Sheri Higgins Law, PLLC; Sheri Higgins

(57) ABSTRACT

Oil-based drilling fluids can include an emulsifier to help stabilize the phases of the fluid. During repeated use, the amount of free emulsifier can become depleted. A field test can be used to determine the amount of free emulsifier in the fluid. Top oil from an aliquot from the fluid can be placed into a testing vial and mixed with an aqueous solution including a dye and optionally a pH adjuster or an acid or acidic buffer to facilitate dye transfer from the aqueous phase to the oil phase. The amount of dye transferred to the oil phase can be used to determine the amount of free emulsifier. Reference samples can be prepared with a known concentration of the emulsifier to visually compare the amount of dye transfer in the testing vial to the reference sample. Spectroscopy can also be used to compare the dye transfer in the test vial to the reference sample.

18 Claims, 10 Drawing Sheets
(9 of 10 Drawing Sheet(s) Filed in Color)

A B C D E

A B C D

A B C D E

A B C D E F G

A B C D E F G H I J

A B C

A B C D

FIELD TEST FOR DETERMINING CONCENTRATION OF EMULSIFIERS IN DRILLING FLUIDS USING DYES

TECHNICAL FIELD

A field test can be used to determine the amount of emulsifier available in an oil-based drilling mud. The test can include adding a dye to a sample of the drilling fluid and visually observing whether the dye has been transported from a water phase to an oil phase, which would indicate the presence of available emulsifier present in the drilling fluid.

BRIEF DESCRIPTION OF THE FIGURES

The patent or application file contains at least one drawing executed in color. Copies of this patent or patent application publication with color drawing(s) will be provided by the Office upon request and payment of the necessary fee.

The features and advantages of certain embodiments will be more readily appreciated when considered in conjunction with the accompanying figures. The figures are not to be construed as limiting any of the preferred embodiments.

DETAILED DESCRIPTION

Figures 1A, 1B, 1C, 1D, 1E, 1F:
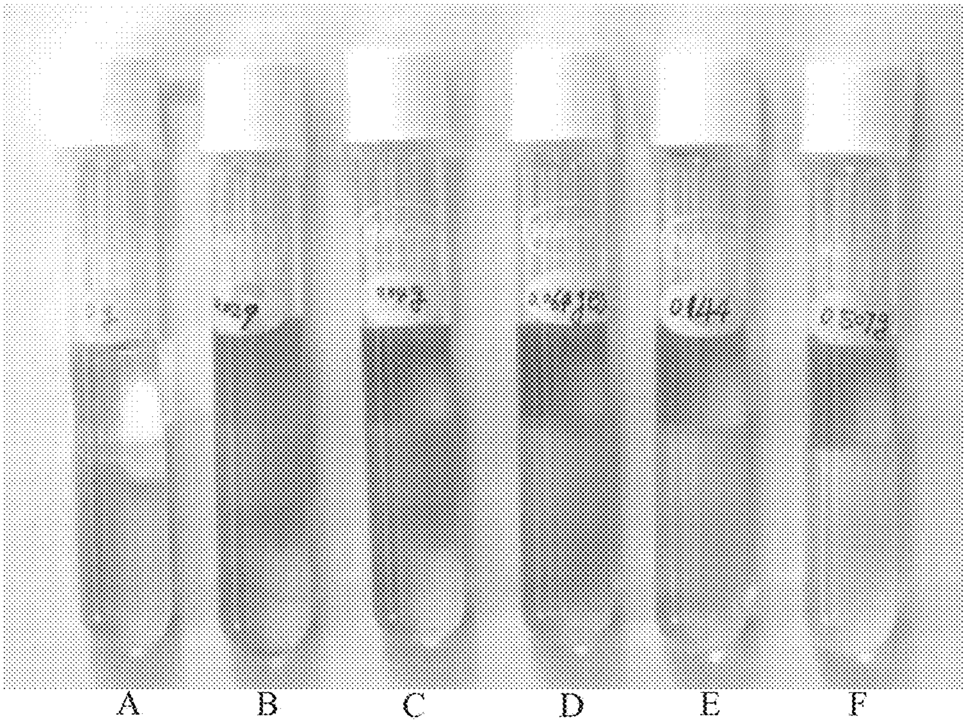
FIGS. 1A-1F are photographs of an invert emulsion with varying concentrations of an emulsifier showing dye transfer.

Oil and gas hydrocarbons are naturally occurring in some subterranean formations. In the oil and gas industry, a subterranean formation containing oil and/or gas is referred to as a reservoir. A reservoir can be located under land or offshore. Reservoirs are typically located in the range of a few hundred feet (shallow reservoirs) to a few tens of thousands of feet (ultra-deep reservoirs). In order to produce oil or gas, a wellbore is drilled into a reservoir or adjacent to a reservoir. The oil, gas, or water produced from a reservoir is called a reservoir fluid.

As used herein, a "fluid" is a substance having a continuous phase that can flow and conform to the outline of its container when the substance is tested at a temperature of 71° F. (22° C.) and a pressure of one atmosphere "atm" (0.1 megapascals "MPa"). A fluid can be a liquid or gas. A homogenous fluid has only one phase; whereas a heterogeneous fluid has more than one distinct phase. A colloid is an example of a heterogeneous fluid. A heterogeneous fluid can be a slurry, which includes a continuous liquid phase and undissolved solid particles as the dispersed or discontinuous phase; an emulsion, which includes a continuous liquid phase and at least one dispersed phase of immiscible liquid droplets; a foam, which includes a continuous liquid phase and a gas as the dispersed phase; or a mist, which includes a continuous gas phase and liquid droplets as the dispersed phase. As used herein, the term "base fluid" means the solvent of a solution or the continuous phase of a heterogeneous fluid and is the liquid that is in the greatest percentage by volume of a treatment fluid. An emulsion has a continuous phase of water and immiscible liquid oil droplets as the dispersed or discontinuous phase or has a continuous phase of an oil and immiscible liquid water droplets as the dispersed or discontinuous phase. When naming an emulsion type, the first letter is the discontinuous phase. Accordingly, O/W is oil in water and is classified as an "emulsion"; whereas W/O is water in oil and is classified as an "invert emulsion".

A well can include, without limitation, an oil, gas, or water production well, an injection well, or a geothermal well. As used herein, a "well" includes at least one wellbore. A wellbore can include vertical, inclined, and horizontal portions, and it can be straight, curved, or branched. As used herein, the term "wellbore" includes any cased, and any uncased, open-hole portion of the wellbore. A near-wellbore region is the subterranean material and rock of the subterranean formation surrounding the wellbore. As used herein, a "well" also includes the near-wellbore region. The near-wellbore region is generally considered to be the region within approximately 100 feet (30.5 meters) radially of the wellbore. As used herein, "into a subterranean formation" means and includes into any portion of the well, including into the wellbore, into the near-wellbore region via the wellbore, or into the subterranean formation via the wellbore.

A portion of a wellbore can be an open hole or cased hole. In an open-hole wellbore portion, a tubing string can be placed into the wellbore. The tubing string allows fluids to be introduced into or flowed from a remote portion of the wellbore. In a cased-hole wellbore portion, a casing is placed into the wellbore that can also contain a tubing string. A wellbore can contain an annulus. Examples of an annulus include but are not limited to the space between the wellbore and the outside of a tubing string in an open-hole wellbore; the space between the wellbore and the outside of a casing in a cased-hole wellbore; and the space between the inside of a casing and the outside of a tubing string in a cased-hole wellbore.

Oil or gas operations can be performed using a treatment fluid. The term "treatment fluid" refers to the specific composition of the fluid as it is being introduced into a well. The word "treatment" in the term "treatment fluid" does not necessarily imply any particular action by the fluid. Examples of treatment fluids include, but are not limited to, drilling fluids, spacer fluids, workover fluids, cement compositions, and stimulation fluids.

During drilling operations, a wellbore is formed using a drill bit. A drill string can be used to aid the drill bit in drilling through a subterranean formation to form the wellbore. The drill string can include a drilling pipe. A treatment fluid adapted for this purpose is referred to as a drilling fluid or drilling mud. The wellbore defines a wellbore wall that is the exposed portion of the subterranean formation where the wellbore was formed. The drilling fluid may be circulated downwardly through the drilling pipe and back up the annulus between the wellbore wall and the outside of the drilling pipe.

The drilling fluid performs various functions, such as cooling the drill bit, maintaining the desired pressure in the well, and carrying drill cuttings upwardly through the annulus between the wellbore and the drilling pipe. Accordingly, a drilling fluid can possess desirable properties, such as viscosity or pumpability, in order to perform the various functions. To impart desirable properties to the drilling fluid, additives can be included in the fluid. One example of an additive is an emulsifier.

An emulsifier and a surfactant can have similar structures. While all emulsifiers can be classified as a surfactant, not all surfactants are emulsifiers. Emulsifiers generally stabilize a dispersion of an insoluble discontinuous phase (internal phase) in a continuous phase (external phase). Emulsifiers and surfactants are amphiphilic molecules comprising a hydrophobic tail group and a hydrophilic head group. The hydrophilic head can be charged. Emulsifiers and surfactants can lower the interfacial tension between two liquids or between a solid and a liquid. Emulsifiers and surfactants can also be used to change the wettability of the surface of solids of a formation. Wettability means the preference of a surface to be in contact with one liquid or gas rather than another. Accordingly, "oil-wet" means the preference of a surface to be in contact with an oil phase or gas phase rather than a water phase, and "water-wet" means the preference of a surface to be in contact with a water phase rather than an oil phase or gas phase. Emulsifiers and surfactants can be used to change the wettability of the surface of the solids from being water-wet to being oil-wet or vice versa.

If an emulsifier is in a sufficient concentration in a solution, then the emulsifier molecules can form micelles. A "micelle" is an aggregate of emulsifier molecules dispersed in a solution. An emulsifier in an aqueous solution can form micelles with the hydrophilic heads in contact with the surrounding aqueous solvent, sequestering the hydrophobic tails in the micelle center. A micelle in a hydrocarbon solution forms with the hydrophobic tails in contact with the hydrocarbon solution, sequestering the hydrophilic heads in the center of the micelle. The emulsifier must be in a sufficient concentration to form micelles, known as the critical micelle concentration (CMC). The critical micelle concentration is the concentration of emulsifier above which micelles are spontaneously formed.

The hydrophilic-lipophilic balance ("HLB") of the emulsifier can be used to determine whether an emulsion forms as a water-in-oil or an oil-in-water emulsion. HLB is a measure of the degree to which an emulsifier is hydrophilic or lipophilic. One formula that can be used to calculate HLB is listed below as equation 1.

$$HLB = 20 * Mh/M \qquad \text{Eq. 1}$$

where Mh is the molecular mass of the hydrophilic portion of the emulsifier; and M is the molecular mass of the emulsifier as a whole. The HLB can be used to define whether a compound functions as an emulsifier to keep the dispersed phase properly dispersed throughout the continuous oil phase and provide stability to the dispersed phase or whether the compound functions as a surfactant. Generally, a compound can function as, and therefore be categorized, as an emulsifier if the HLB of the compound is greater than 3.

Drilling fluids are prepared prior to beginning the drilling operation. A known concentration of additives, such as emulsifiers, are added to the fluid. However, drilling operations generally take hours, days, or even weeks to complete. During the drilling operation, the drilling fluid is circulated within the wellbore and back up to the surface where the fluid is cycled through solids removal equipment to remove drill cuttings among other things and recycled back into the wellbore. A drilling fluid can also be re-used at multiple job sites and recycled for months or even years. The concentration of the additives generally decreases during continued use of the drilling fluid. Depletion of emulsifiers can mean that there is no longer a sufficient amount of the emulsifier to provide stability to the phases of an emulsion or invert emulsion or alter the wettability as needed. Fluids heavily laden with strengthening materials such as lost-circulation particulates can further deplete the wetting capability of emulsifiers. A fluid with too little emulsifier risks poor performance, for example "sagging" of other additives such as weighting agents and may lack adequate phase stability. A fluid with too much emulsifier can be more costly because more additive than needed is added, and the excess can also damage the subterranean formation and alter the reservoir wettability. The excess emulsifier can make the entire reservoir oil wet and give false readings on the reservoir content, which can make conclusive formation evaluation difficult when conducting exploratory drilling.

In order to maintain optimal concentrations of emulsifiers, a sample of the drilling fluid can be tested. Currently, the sample must be sent offsite to a laboratory where testing such as mass spectrometry or Fourier transform infrared (FTIR) spectroscopy can be performed because the size of testing equipment may be too large for onsite testing. Accordingly, there is an increased cost in having to ship the samples to the laboratory and a delay in the drilling operation while awaiting the results. There are also current procedures that are used to estimate the concentration of emulsifiers in the drilling fluid at the wellsite. The concentration of free emulsifier in an oil-based drilling mud has traditionally been estimated at the wellsite from the appearance of the surface of the mud. Shiny surfaces indicated a sufficient concentration of emulsifier whereas "grainy" surfaces were an indication of an insufficient concentration. This approach is very subjective and does not provide any way to quantify with any accuracy the concentration of the emulsifier. Kjeldahl nitrogen measurements can also give an estimation of the total nitrogen in a mud, though this procedure does not provide an indication of whether the emulsifier has been degraded or it is in a "healthy" state to provide the necessary functionality nor is the test selective for emulsifiers.

It has been discovered that the amount of free emulsifier in a drilling fluid can be determined at the well site by using a dye transfer test. The dye transfer test can include observing the amount of dye that transfers from a water phase of an aqueous solution containing the dye to the oil phase of the drilling fluid. In order to simplify the determination and make this phase transfer easier to see, extracted hydrocarbon phase or base fluid from the drilling fluid can be utilized. The extracted hydrocarbon phase can be obtained from centrifugation of the fluid to yield a separated continuous phase on the top of the fluid (top oil), or by use of a filtration process which restricts the flow of particles in the fluid and only allows base oil-rich filtrate (along with the emulsifier molecules/micelles, if present) to be extracted.

A system for determining an amount of free emulsifier in a drilling fluid can include an amount of top oil from an aliquot of the drilling fluid, wherein the drilling fluid comprises a base oil, an aqueous phase, and an emulsifier; an amount of an aqueous solution comprising water and a dye at a concentration by weight percent of the water; a testing vial, wherein the testing vial is configured to receive the amount of top oil and the amount of the aqueous solution; and a reference sample vial containing an amount of an oil with a known concentration of the emulsifier and an amount of an aqueous solution comprising water and the dye at the concentration by weight percent of the water.

A method for determining an amount of free emulsifier in a drilling fluid can include obtaining an aliquot of the drilling fluid, wherein the drilling fluid comprises a base oil, an aqueous phase, and an emulsifier; obtaining top oil from the aliquot; preparing an aqueous solution comprising water and a dye at a concentration by weight percent of the water; placing an amount of the top oil and an amount of the aqueous solution into a testing vial; preparing a reference sample by placing an amount of an oil with a known concentration of the emulsifier and an amount of an aqueous solution comprising water and the dye at the concentration by weight percent of the water into a reference sample vial; and evaluating an amount of dye transferred from the aqueous solution phase to the top oil phase in the testing vial against an amount of dye transferred from the aqueous solution phase to the oil phase in the reference sample vial.

It is to be understood that the discussion of any of the embodiments regarding the testing procedure or any ingredients in the testing vial or the reference sample vial are intended to apply to all of the system and method embodiments without the need to repeat the various embodiments throughout. Any reference to the unit "gallons" means U.S. gallons.

An aliquot of the drilling fluid can be obtained, for example, by collecting some of the drilling fluid at the well site for testing. The drilling fluid can be a water in oil invert emulsion. The drilling fluid includes a base fluid. The base fluid can include dissolved materials or undissolved solids. The base fluid can include a hydrocarbon liquid oil as the continuous phase of the invert emulsion. The oil can be selected from the group consisting of a fractional distillate of crude oil; a fatty derivative of an acid, an ester, an ether, an alcohol, an amine, an amide, or an imide; a saturated hydrocarbon; an unsaturated hydrocarbon; a branched hydrocarbon; a cyclic hydrocarbon; and any combination thereof. Crude oil can be separated into fractional distillates based on the boiling point of the fractions in the crude oil. An example of a fractional distillate of crude oil is diesel oil. The saturated hydrocarbon can be an alkane or paraffin. The paraffin can be an isoalkane (isoparaffin), a linear alkane (paraffin), or a cyclic alkane (cycloparaffin). The unsaturated hydrocarbon can be an alkene, alkyne, or aromatic. The alkene can be an isoalkene, linear alkene, or cyclic alkene. The linear alkene can be a linear alpha olefin or an internal olefin.

The drilling fluid can include an aqueous phase including water. The water can be the dispersed or discontinuous phase of the invert emulsion. The water can be selected from the group consisting of freshwater, seawater, brine, and any combination thereof in any proportion. The drilling fluid can include other ingredients, such as lime, weighting agents, and/or a water-soluble salt. The water-soluble salt can be selected from the group consisting of sodium chloride, calcium chloride, calcium bromide, potassium chloride, potassium bromide, magnesium chloride, sodium formate, potassium formate, cesium formate, zinc bromide, and any combination thereof.

The drilling fluid can include an emulsifier. As discussed above, the amount of free emulsifier can become depleted through continued use of the drilling fluid as the emulsifier becomes bound to ingredients in the drilling fluid, lost into permeable areas of the subterranean formation, or bound to solid surfaces of the wall of the wellbore. As used herein, the term "free emulsifier" means the amount of emulsifier that is available to function as an emulsifier (i.e., provides stability to the phases of an emulsion or invert emulsion or alters the wettability of solids). Accordingly, while "the drilling fluid" comprises the base fluid, water, and an emulsifier, it is to be understood that at the time of testing, the amount of free emulsifier may be zero even though the drilling fluid included the emulsifier at some point before testing is performed. In other words, the emulsifier originally included in the drilling fluid may become depleted during use or repeated use of the drilling fluid.

The emulsifier included in the drilling fluid to be tested can be a polyamide emulsifier. As discussed below in the examples section, oxidized tall oil emulsifiers or tall oil fatty acid emulsifiers may not provide accurate results of dye transfer from the water phase to the oil phase. The emulsifier can have a hydrophilic/lipophilic balance (HLB) greater than 3 or greater than 4. The emulsifier can have an HLB in the range of 3 to 6.

Top oil can be obtained from the aliquot of the drilling fluid. As used herein, the term "top oil" means the oil phase from the aliquot that is separated from the water phase. The top oil can be obtained from the aliquot by any of the following methods: allowing the aliquot to settle within a collections container and withdrawing the top oil that has floated to the top of the container, for example via a pipette; centrifuging the aliquot to separate the top oil from the water phase; or filtering the aliquot through a filter paper. Centrifugation can be performed at a speed in the range of 20 to 2,000 revolutions per minute for example. The filter paper can have a pore size in the range of 2 micrometers (μm) to 20 millimeters (mm).

An aqueous solution comprising water and a dye at a concentration by weight of the water can be prepared. The water can be deionized water, fresh water, or water containing a water-soluble salt. The aqueous solution can also include other ingredients, such as but not excluding, a pH adjuster, an acid, or an acidic buffer. The dye can be a water-soluble dye. Examples of dyes that can be used include, but are not limited to, fluorescein, Brilliant-Yellow, Bromocresol-Green, sodium 1,2-naphthoquinone-4-sulfonate, Thymol-Blue, Bromophenol Blue, or Clayton-Yellow. The dye can be in the form of a sodium salt of the dye to increase the dye's water solubility. The chemical structures of the dyes or sodium salts of the dyes are provided below.

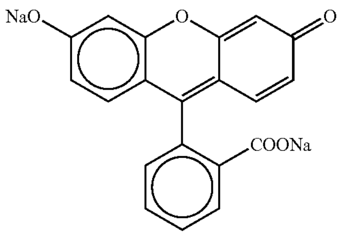

fluorescein sodium salt

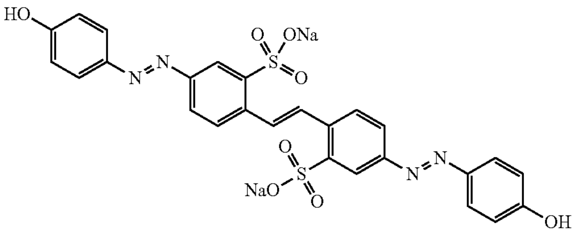

Brilliant-Yellow sodium salt

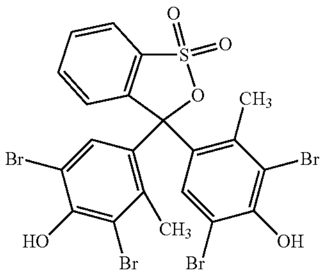

Bromocresol-Green

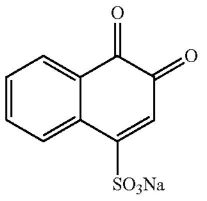

sodium 1,2-naphthoquinone-4-sulfonate

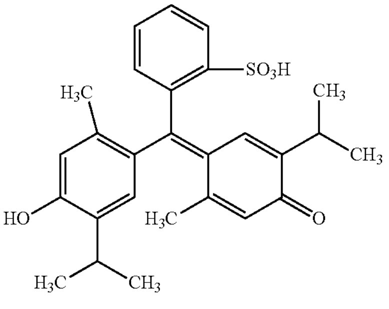

Thymol-Blue

-continued

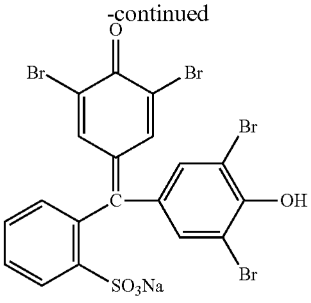

Bromophenol-Blue

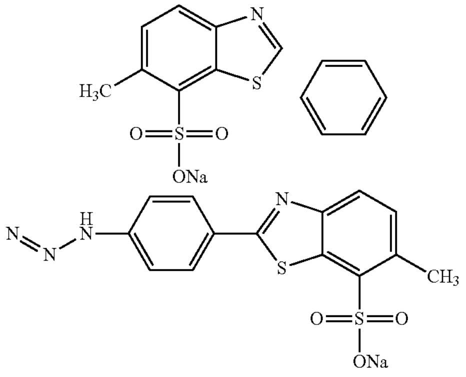

Clayton-Yellow

The dye is included in the aqueous solution at a concentration by weight percent (wt %) of the water. The concentration of the dye can be selected such that any free emulsifier present in the top oil of the aliquot can be detected by transference of the dye from the aqueous phase to the top oil phase. The concentration of the dye can also be used to quantify the amount of free emulsifier when compared to a reference sample. For example, the dye can be in a concentration in a range of 0.1 to 5 wt %.

As discussed above, the aqueous solution can also include a pH adjuster, an acid, or an acidic buffer. The pH adjuster can be selected to adjust the pH of the aqueous solution to a desired pH. Dye transfer from the aqueous phase to the top oil phase may be dependent on the pH. The desired pH of the aqueous solution can be a pH that allows the dye to transfer. By way of example, the desired pH of the aqueous solution can be in a range of 5 to 11. If the pH of the dye used is less than the desired pH, then a base, for example sodium hydroxide (NaOH), can be used to increase the pH of the aqueous solution. The concentration of the pH adjuster can be selected to provide the desired pH to the aqueous solution.

Other ingredients in the drilling fluid aliquot, for example water-soluble salts, lime, or weighting agents, can have a negative effect on the capability of the dye to transfer from the aqueous solution to the top oil. To counteract these negative effects, an acid or an acidic buffer can be included in the aqueous solution. The acid can be for example acetic acid or hydrochloric acid. The acid can be selected such that it is less toxic or harmful to personnel than other types of acids that could be used. The acidic buffer can be for example equal moles of acetic acid and sodium acetate. Whether to use an acid or acidic buffer can depend on the type of dye used in the aqueous solution. The concentration of the acid or acidic buffer can be selected such that a reference sample provides the ability of the emulsifier to transfer the dye from the water phase to the oil phase. The concentration of the acid or acidic buffer can be, for example, in the range of 0.001 to 3 wt % of the water.

An amount of the top oil from the aliquot can be placed within a testing vial. The vial can be cylindrical in shape, have a variety of dimensions, and can have a flat or curved bottom. The testing vial should be made from a transparent material such as glass or plastic to enable visual observations to be made. The amount of top oil added to the testing vial can vary and can be selected based on the dye used and a known concentration of emulsifier and/or known concentration of oil used in a reference sample. By way of example, the amount of top oil from the aliquot added to the testing vial can range from 0.5 to 10 grams (g). As discussed above, the top oil can be centrifuged and/or filtered prior to being placed within the testing vial.

An amount of the aqueous solution containing the dye at the desired concentration is also placed within the testing vial. As discussed above, the aqueous solution can further include a pH adjuster, an acid, or an acidic buffer. The amount of the aqueous solution can be the same or different from the amount of the top oil. Preferably, the amount of the aqueous solution is greater than the amount of the top oil. By way of example, the amount of the aqueous solution can be 2 times, 3 times, or up to 10 times greater than the amount of the top oil.

After the top oil and the aqueous solution have been added to the testing vial, the vial can be shaken by hand or on a mixer to mix the water phase and oil phase together. The testing vial can then be placed stationary anywhere from 1 minute to 1 hour for example, to allow any of the free emulsifier in the top oil to transport the dye from the water phase to the oil phase. An evaluation can then be made on the amount of dye that is transferred from the water phase to the oil phase, which can be used to determine the amount of free emulsifier in the drilling fluid. Visual observation can be used to evaluate how much if any of the dye transfers. Even if none or very little of the dye transfers to the oil phase, it does not necessarily mean that there is not free emulsifier in the top oil. As discussed above, the pH or ingredients in the aliquot such as lime can provide a false result. Therefore, a pH adjuster, an acid, or an acid buffer can be added to the testing vial to determine if such a situation is present. Alternatively, a second, third, fourth, or so on test can be performed with varying adjustments to the pH and/or concentration of an acid or acidic buffer. The pH of the aqueous solution can also be measured before placement into the testing vial to determine if a pH adjuster needs to be added to obtain the desired pH-depending, in part, on the specific dye selected and the optimum pH for that specific dye.

If a desired amount of the dye is transferred to the oil phase, then additional emulsifier may not need to be added to the drilling fluid. However, if less than the desired amount of the dye is transferred, this can indicate that there is an insufficient amount of free emulsifier in the drilling fluid. In this case, incremental amounts of the emulsifier used in the drilling fluid can be added to the testing vial until the desired amount of the dye is transferred to the oil phase. Calculations can then be performed to scale up the concentration of emulsifier that is needed to add to the drilling fluid. The concentration of emulsifier needed in the drilling fluid can be determined based on the specifics of the subterranean formation being drilled and other desirable properties of the drilling fluid.

Determining the amount of dye transfer can also be performed using spectroscopy. The amount of free emulsifier can be compared quantitatively using a spectrophotometer or similar instrument to measure the absorbance at different wavelengths. Absorbance of the dye that is transferred in the test vial can be compared to a calibration curve generated from known concentrations of dye in reference samples using Beer's Law. At each incremental addition of emulsifier to the testing vial, the absorbance should increase. In this manner, it is possible to correlate the absorbance to the concentration of free emulsifier in the fluid. A given absorbance can be used to determine the concentration of free emulsifier and how much more emulsifier may need to be added can be calculated. By way of example, if a test sample has an absorbance of 1, then when compared to the calibration curve can indicate the amount of free emulsifier is 2 ppb, and an absorbance of 3 can correlated to a concentration of 6 ppb.

The concentration of free emulsifier in the drilling fluid can also be determined by preparing one or more reference samples in reference sample vials. The reference samples can be prepared with an amount of an oil (which can be chemically the same or similar to the base oil in the drilling fluid) with known concentrations of the emulsifier mixed with an amount of an aqueous solution including the same dye and optional pH adjuster, acid, or acidic buffer. The reference samples can be identical to the testing samples with the only difference being the concentration of the emulsifier. The concentration of the dye in the reference samples can be the same or different from the concentration in the testing vial. If more than one reference sample is prepared, then the concentration of emulsifier that is added to the oil can increase in desired increments. If more than one reference sample is prepared, then preferably the concentration of emulsifier added to each of the reference sample vials is within a low to high range of the desired concentration of free emulsifier needed in the drilling fluid. By way of example, if the amount of free emulsifier needed in the specific drilling fluid to be tested is in a range from 2 to 10 pounds per barrel (ppb), then a first reference sample can be prepared corresponding to the low end of the range of 2 ppb, and a second reference sample can be prepared corresponding to the high end of the range of 10 ppb.

A visual comparison of the amount of dye transferred from the aqueous solution phase to the top oil phase in the testing vial can be made against the amount of dye transferred from the aqueous solution phase to the oil phase in the reference sample vial(s). In this manner, an estimation of the concentration of free emulsifier in the drilling fluid can be made. The pH of the reference sample can be the same as the pH of the aqueous solution in the testing vial. In this manner, a direct comparison can be made without the pH effecting the capability of dye transfer.

An embodiment of the present disclosure is a system for determining an amount of free emulsifier in a drilling fluid comprising: an amount of top oil from an aliquot of the drilling fluid, wherein the drilling fluid comprises a base oil, an aqueous phase, and an emulsifier; an amount of an aqueous solution comprising water and a dye at a concentration by weight percent of the water; and a testing vial, wherein the testing vial is configured to receive the amount of top oil and the amount of the aqueous solution. Optionally, the emulsifier is a polyamide emulsifier. Optionally, the emulsifier has a hydrophilic/lipophilic balance greater than 3. Optionally, the water is selected from deionized water, fresh water, or water containing a water-soluble salt. Optionally, the dye is a water-soluble dye selected from fluorescein, Brilliant-Yellow, Bromocresol-Green, sodium 1,2-naphthoquinone-4-sulfonate, Thymol-Blue, Bromophenol Blue, or Clayton-Yellow. Optionally, the dye is in a concentration in a range of 0.1 to 5 wt % of the water. Optionally, the aqueous solution further comprises a pH adjuster, an acid, or an acidic buffer. Optionally, the aqueous solution has a pH in a range of 5 to 11. Optionally, the amount of top oil from the aliquot is in a range from 0.5 to 10 grams. Optionally, the amount of the aqueous solution is greater than the amount of the top oil. Optionally, the system further comprises a reference sample vial containing an amount of an oil with a known concentration of the emulsifier and an amount of an aqueous solution comprising water and the dye at a concentration by weight percent of the water.

Another embodiment of the present disclosure is a method for determining an amount of free emulsifier in a drilling fluid comprising: obtaining an aliquot of the drilling fluid, wherein the drilling fluid comprises a base oil, an aqueous phase, and an emulsifier; obtaining top oil from the aliquot; preparing an aqueous solution comprising water and a dye at a concentration by weight percent of the water; placing an amount of the top oil and an amount of the aqueous solution into a testing vial; and evaluating an amount of the dye transferred from the aqueous solution phase to the top oil phase in the testing vial to determine the amount of free emulsifier in the drilling fluid. Optionally, the emulsifier is a polyamide emulsifier. Optionally, the emulsifier has a hydrophilic/lipophilic balance greater than 3. Optionally, the water is selected from deionized water, fresh water, or water containing a water-soluble salt. Optionally, the dye is a water-soluble dye selected from fluorescein, Brilliant-Yellow, Bromocresol-Green, sodium 1,2-naphthoquinone-4-sulfonate, Thymol-Blue, Bromophenol Blue, or Clayton-Yellow. Optionally, the dye is in a concentration in a range of 0.1 to 5 wt % of the water. Optionally, the aqueous solution further comprises a pH adjuster, an acid, or an acidic buffer. Optionally, the aqueous solution has a pH in a range of 5 to 11. Optionally, the amount of top oil from the aliquot is in a range from 0.5 to 10 grams. Optionally, the amount of the aqueous solution is greater than the amount of the top oil. Optionally, the top oil is obtained from the aliquot by allowing the aliquot to settle within a collections container and withdrawing the top oil that has floated to the top of the container; centrifuging the aliquot to separate the top oil from the aqueous phase; or filtering the aliquot through a filter paper. Optionally, the filter paper has a pore size in a range of 2 micrometers to 20 millimeters. Optionally, the method further comprises mixing the top oil and the aqueous solution in the testing vial after the top oil and the aqueous solution have been placed in the testing vial; and allowing the testing vial to remain stationary to allow any of the free emulsifier in the top oil to transport the dye from the aqueous solution to the top oil. Optionally, the method further comprises preparing a reference sample by placing an amount of the base oil of the drilling fluid with a known concentration of the emulsifier and an amount of an aqueous solution comprising water and the dye at a concentration by weight percent of the water into a reference sample vial. Optionally, the method further comprises visually comparing the amount of the dye transferred from the aqueous solution phase to the top oil phase in the testing vial against an amount of dye transferred from the aqueous solution phase to the base oil phase in the reference sample vial to determine the amount of free emulsifier. Optionally, the method further comprises adding incremental amounts of the emulsifier in the drilling fluid to the testing vial until a desired amount of the dye is transferred to the top oil phase while visually comparing against the amount of dye transferred in the reference sample vial. Optionally, the method further comprises measuring an absorbance of the dye transferred to the top oil in the testing vial; measuring an absorbance of the dye transferred to the base oil in the reference sample vial; and comparing the absorbance from the testing vial against the absorbance from the reference sample vial. Optionally, the method further comprises preparing more than one reference sample, wherein each of the reference samples are identical except for a different concentration of the emulsifier; generating a calibration curve from an absorbance from each of the reference samples; and comparing the absorbance from the testing vial to the calibration curve.

EXAMPLES

To facilitate a better understanding of the various embodiments, the following examples are given. The following examples were used to evaluate dye transfer from a dispersed water phase to a continuous oil phase of an invert emulsion W/O drilling fluid.

To find out how the emulsifier affects the partitioning of fluorescein dye in the water and oil phases, a series of samples each of which consisted of 4 grams (g) of a blend of cyclic and n-alkanes oil, varying concentrations of a polyamide emulsifier, and 10 g of an aqueous solution consisting of deionized water and fluorescein dye at a concentration of 0.1 wt % were prepared. The samples shown in FIGS. 1A-1F, from left to right, included increasing concentrations of the polyamide emulsifier of 0 g, 0.029 g. 0.04 g. 0.064 g. 0.114 g, and 0.507 g. respectively, that were added to the tubes, and the tubes were shaken vigorously by hand to allow dye distribution equilibrium to be reached. To separate the emulsion that formed, the tubes were centrifuged. The pictures of the six samples were taken soon after centrifugation.

Figure 2:
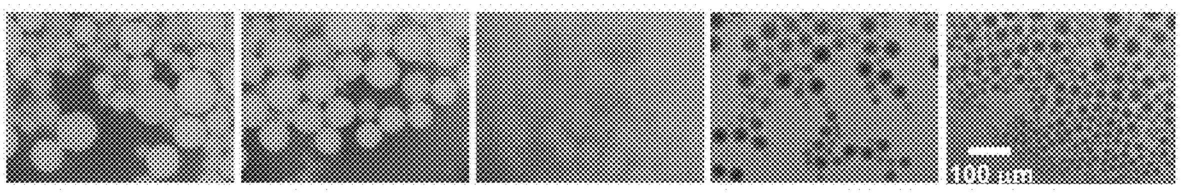
FIG. 2 are micrographs of the invert emulsions of FIGS. 1B-1F.

As can be seen in FIG. 1A of the sample that did not include any of the emulsifier, the fluorescein dye remained completely in the water phase and did not transfer to the oil phase. As the concentration of the emulsifier increased, more of the dye transferred from the water phase at the bottom of the tube to the oil phase at the top of the tube, where at a concentration of 0.507 g of the emulsifier in FIG. 1F, almost all of the dye transferred from the water phase to the oil phase. The process of fluorescein transferring from the water to oil phase was confirmed in the micrographs of samples from FIG. 1B-1F as shown in FIG. 2. As can be seen in FIG. 2, from left to right, the water drops were initially fluorescent and the background oil phase was darker in color indicating the dye was still mostly in the water phase, but as the concentration of the emulsifier increased from left to right, the water drops became non-fluorescent and the continuous oil phase became more fluorescent.

Figure 3A:
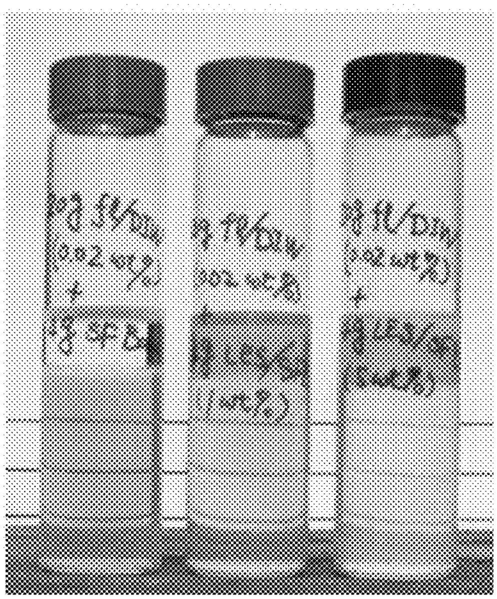
FIGS. 3A-3D are photographs of invert emulsions with different base oils, different emulsifiers, and varying concentrations of the emulsifier.
Figure 3B:
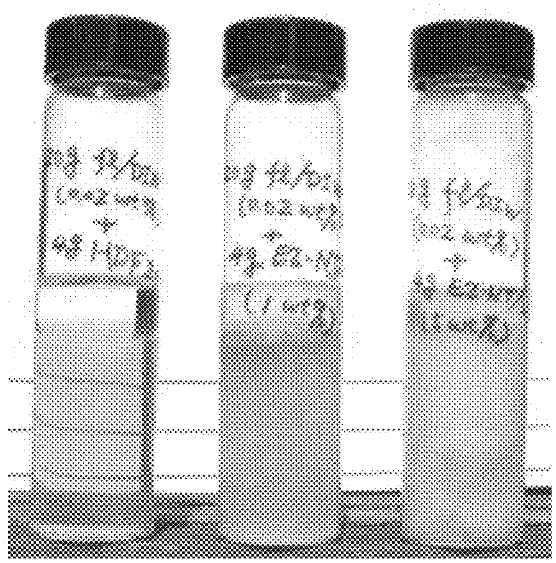
Figure 3C:
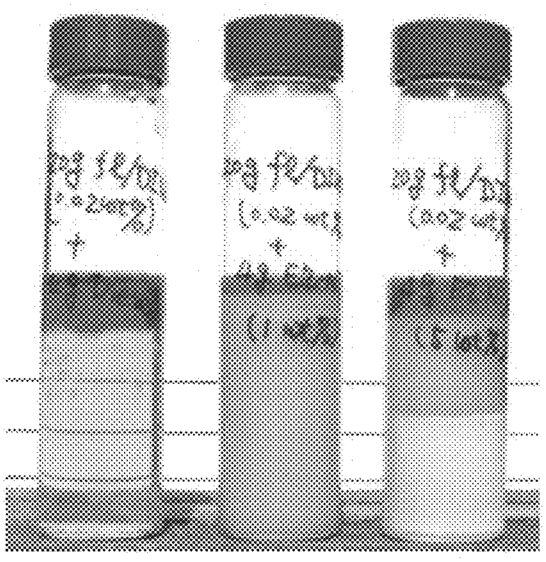

The samples in FIGS. 3A-3D were prepared to evaluate whether fluorescein dye transfer was dependent on the type of oil. In each vial, 20 g of an aqueous solution containing 0.02 wt % fluorescein in deionized water was mixed with 4 g of different base oils and different emulsifiers as follows: FIG. 3A contained an internal olefin base oil with a polyamide emulsifier; FIG. 3B contained a blend of branched and n-paraffins base oil with a polyamide base oil; FIG. 3C contained diesel oil of aromatic and non-aromatic hydrocarbons with a polyamide emulsifier; and FIG. 3D contained diesel oil with a blended emulsifier containing active contents of approximately 50% by volume of an oxidized tall oil and approximately 25% by volume of a polyamide. The mixing was done by vigorous shaking with hand. In each photo, from left to right, the emulsifier was in a concentration of 0, 1, and 5 wt % for FIGS. 3A-3C and 0, 1, and 7.5 wt % for FIG. 3D.

Figure 3D:
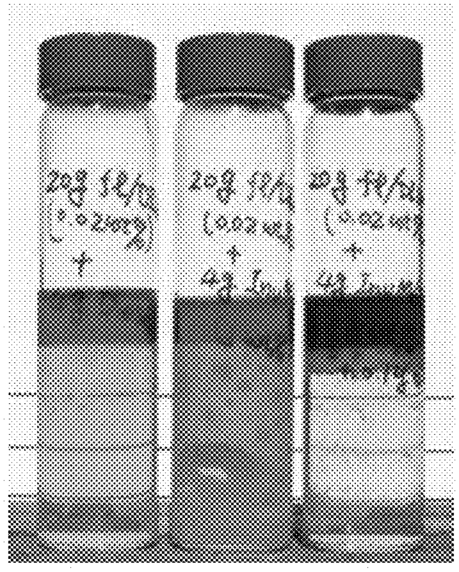
Figure 4A:
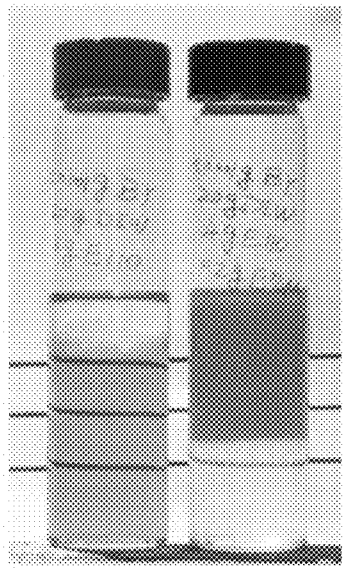
FIGS. 4A-4D are photographs of an invert emulsion with and without an emulsifier showing different dyes.
Figure 4B:
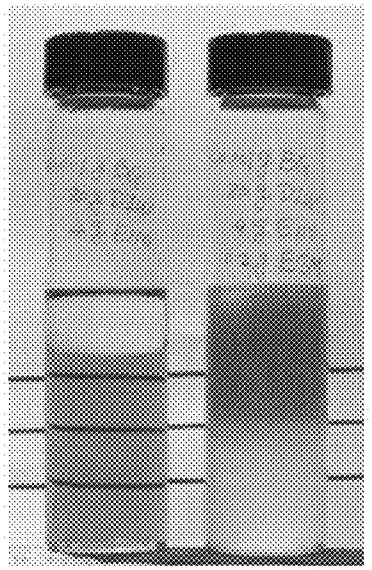
Figure 4C:
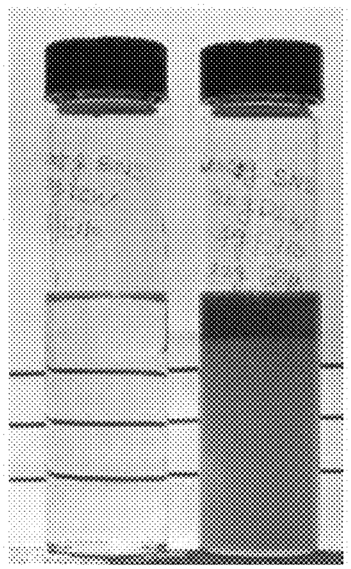
Figure 4D:
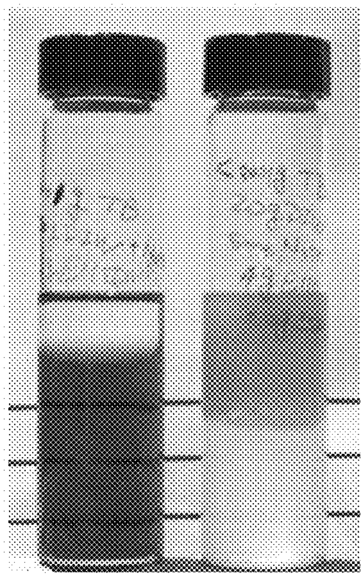

As can be seen in FIG. 3A, adding a polyamide emulsifier into the internal olefin base oil caused dye to transfer from water to oil phase. Especially, at the concentration of 5 wt % emulsifier in the oil, most of the dye transferred to the oil phase so that the bottom water layer went almost colorless. A similar result was obtained as shown in FIGS. 3B and 3C with different base oils. However, for the blended emulsifier as shown in FIG. 3D, most of the dye stayed in the water phase even at the concentration of 7.5 wt %. Amidoamines emulsifiers having an HLB greater than or equal to 5 works very well to transfer the dye out of the water phase; whereas, the oxidized tall oil emulsifier having an HLB in the range of 1-3 did not seem to work well. This indicates that dye transfer performance can be tied to an emulsifier with an HLB greater than 3. Accordingly, the type of emulsifier may have an effect on the amount of dye that transfers from the water phase to the oil phase. In addition, with the concentrations of the dye in water and emulsifier in oil constant, the amounts of oil and water required for the water phase being colorless can be scaled down proportionally.

The samples in FIGS. 4A-4D were prepared to evaluate whether different dyes other than fluorescein would work to indicate emulsifier concentration. In each vial, 20 g of an aqueous solution containing 0.02 wt % of the dye in deionized water was mixed with 4 g of a blended cyclic and n-alkanes oil with vigorous shaking by hand. In each photo, there was no emulsifier in the left tube and 5 wt % polyamide emulsifier in the right tube. The dyes were Brilliant-Yellow for FIG. 4A, Bromocresol-Green for FIG. 4B, sodium 1,2-naphthoquinone-4-sulfonate for FIG. 4C, and Thymol-Blue for FIG. 4D. As can be seen, each of the dyes performed well with a clear dye transfer from the water phase to the oil phase, with the sodium 1,2-naphthoquinone-4-sulfonate dye having a slightly cloudier appearance in the water phase than the other 3 dyes. This indicates that a variety of dyes can be used to evaluate the concentration of emulsifier in a drilling fluid. The color change of the Thymol-Blue from blue to orange in FIG. 4D may be a result of the pH of the fluid.

Figure 5A:
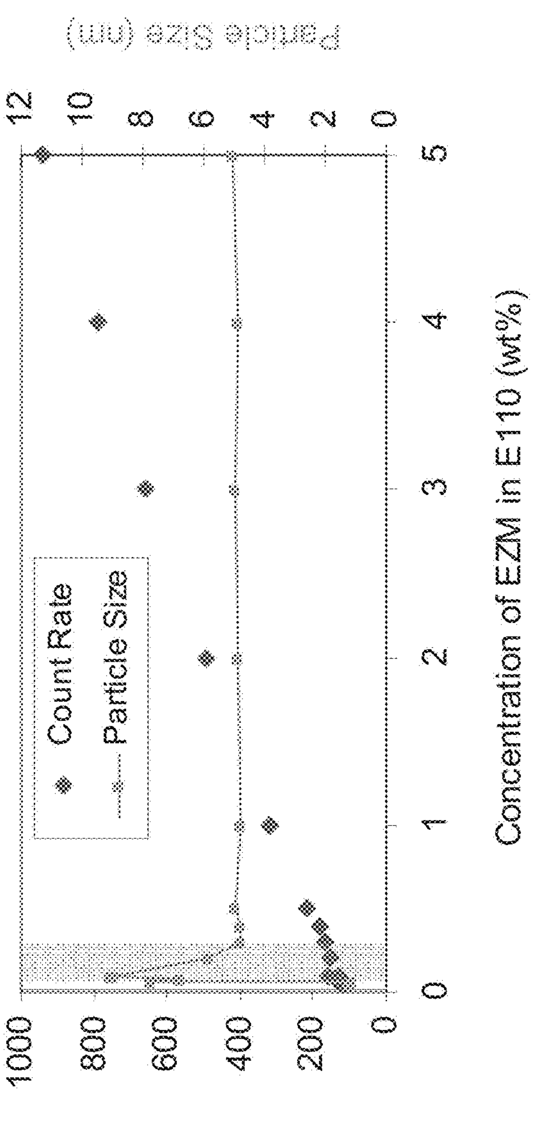
FIG. 5A is a plot of count rate and particle size versus concentration of an emulsifier using dynamic light scattering measurements.
Figure 5B:
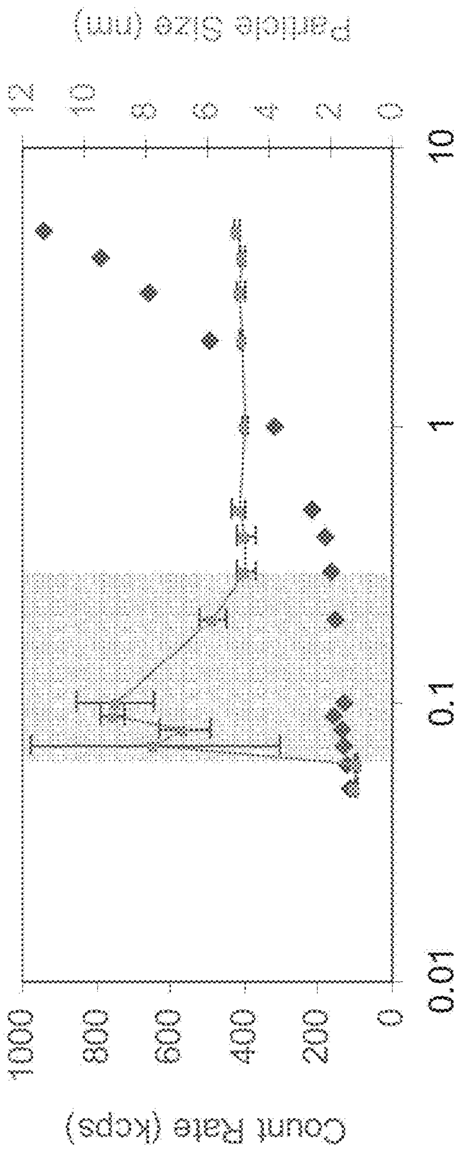
FIG. 5B is a logarithmic plot of the data from FIG. 5A.

To understand how the emulsifier extracts the dyes from the water phase and makes them soluble in the oil, the aggregation status of the emulsifier itself in the base oil was looked at using dynamic light scattering (DLS). In a DLS measurement, by analyzing the time-dependent intensity fluctuation in the scattered light (the interference pattern) from a sample (e.g., an emulsion), both the particle size and the number of particles (proportional to the count rate) in the measured volume can be obtained. FIG. 5A shows the DLS data (the count rate and the particle size) of a polyamide emulsifier in a blended cyclic and n-alkanes oil as a function of emulsifier concentration. FIG. 5B is a re-plot of the data from FIG. 5A on a logarithmic scale. As can be seen, when the concentration of the emulsifier was below 0.06 wt %, the particle size was only ~1.2 nanometers (nm), which is around the molecular size of the active component in the polyamide emulsifier. When the concentration was in the range of 0.06-0.3 wt %, the particles in the sample jumped to a much larger size at ~7-10 nm and the particle size fluctuated strongly from one measurement to another even at the same concentration. When the concentration was above 0.3 wt %, the particle size kept constant at ~5 nm, which is within the size range for micelles to be formed by the emulsifier and the count rate (i.e., the number of particles) increased linearly with the emulsifier concentration. The DLS data suggested that the polyamide emulsifier formed micelles in the base oil at a critical micelle concentration (CMC) of ~0.3 wt %. At a concentration of 0.06-0.3 wt %, a transition region was observed as the concentration neared the CMC. For solutions of the polyamide emulsifier in the blended cyclic and n-alkanes oil (2 and 5 wt %) in equilibrium with deionized water, and for solutions of the emulsifier in the oil (1 and 5 wt %) in equilibrium with aqueous solution of deionized water and fluorescein (0.02 wt %), the particle size was about 5.8-6 nm, which is around 1 nm larger than the micelles formed by the emulsifier alone in the oil. This suggests that some water and/or dye molecules were incorporated into the micelles to form micro-emulsions.

The polyamide emulsifiers worked very well at transferring a variety of different dyes to the oil phase. The active component in the polyamide emulsifiers is the product of reaction of tall oil fatty acid (TOFA), diethylene triamine (DETA), and maleic anhydride (MA).

To evaluate what kind of emulsifiers can make dye-transfer happen, three different emulsifiers were examined. The first was an anionic emulsifier-TOFA (tall oil fatty acid, containing mainly oleic acid), which can lose a proton to be anionic. The other two were non-ionic surfactants-Nonylphenol polyethoxylate and (PEG) 9-Dioleate with chemical structures shown below.

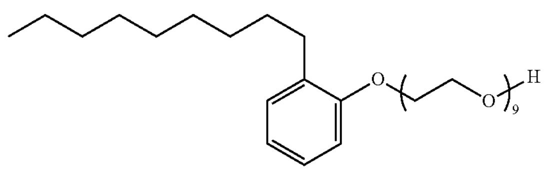

Nonylphenol polyethoxylate

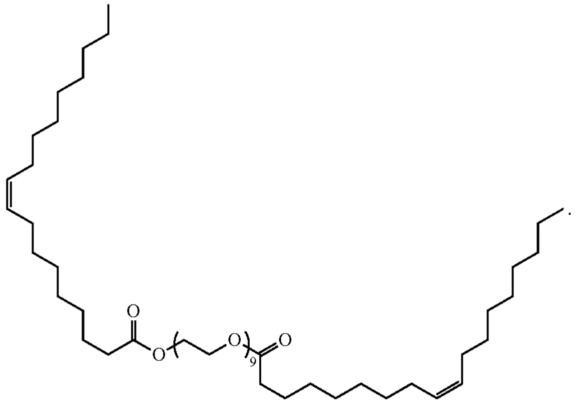

$(PEG)_9$-Dioleate

Figure 6A:
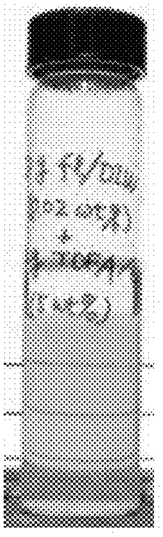
FIGS. 6A-6C are photographs of an invert emulsion with different emulsifiers—namely TOFA, nonylphenol polyethoxylate, and $(PEG)_9$-Diolate, respectively—showing that the dye did not transfer from the water phase to the oil phase.
Figure 6B:
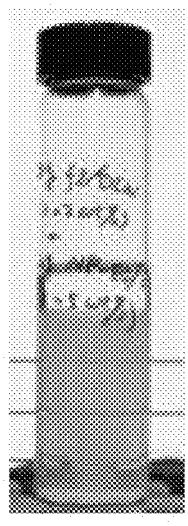
Figure 6C:
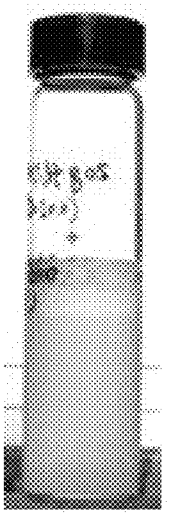
Figures 7A, 7B, 7C, 7D, 7E:
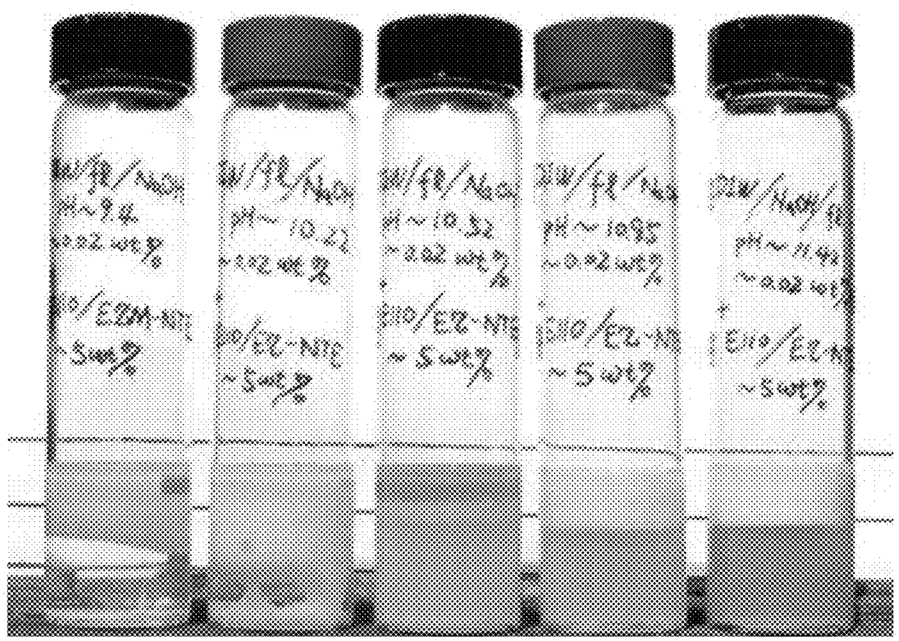
FIGS. 7A-7E are photographs of an invert emulsion showing the effect of pH on fluorescein dye transfer.
Figures 8A, 8B, 8C, 8D:
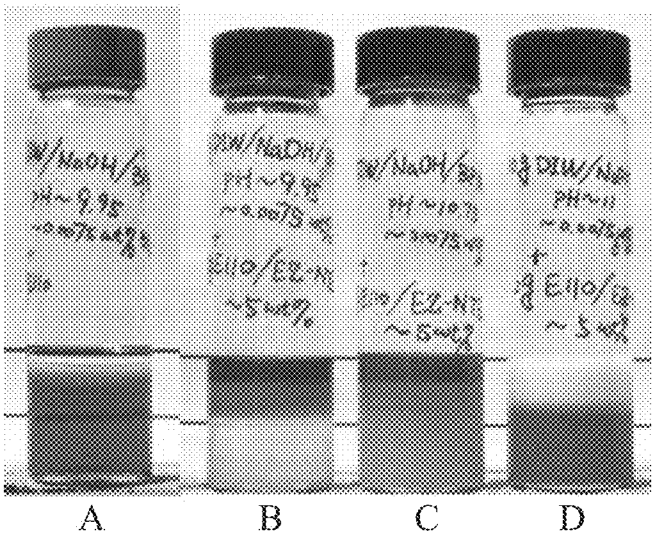
FIGS. 8A-8D are photographs of an invert emulsion showing the effect of pH on bromophenol blue dye transfer.
Figures 9A, 9B, 9C, 9D, 9E:
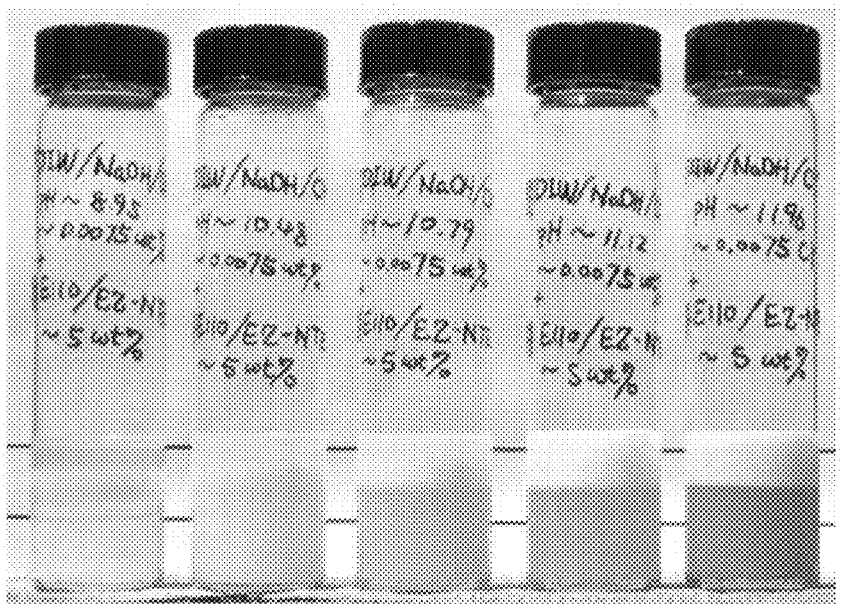
FIGS. 9A-9E are photographs of an invert emulsion showing the effect of pH on Clayton-Yellow dye transfer.

For FIGS. 6A-6C, each vial contained 20 g aqueous solution with 0.02 wt % fluorescein dye in deionized water was mixed with 4 g blended cyclic and n-alkanes oil with 5 wt % of emulsifiers as TOFA for FIG. 6A, Nonylphenol polyethoxylate for FIG. 6B, and $(PEG)_9$-Dioleate for FIG. 6C. As can be seen, the dye did not transfer from the water phase to the oil phase for any of the three emulsifiers. These results seem to suggest that an emulsifier needs to have some amine-like characteristics to cause the dye to transfer from water to oil.

The samples in FIGS. 7A-7E were prepared to evaluate whether the pH of the fluid affected dye transfer. In each vial, 10 g of an aqueous solution 0.02 wt % fluorescein dye in deionized water was mixed with 2 g of a blend of cyclic and n-alkanes oil by vigorous shaking. The only difference among the five samples was the pH, which was adjusted using sodium hydroxide (NaOH) of the water phase wherein the pH increased from left to right as follows: 9.4, 10.22, 10.52, 10.85, and 11.42. After mixing the water and oil phases by vigorous shaking and letting the samples stand, fluorescein transferred to the oil phase at a pH<10.22. At a pH around 10.5, the dye was partially distributed between oil and water. At a pH above 10.8, most of the dye molecules stayed in the water phase. These results suggest that either the dye molecules or the surfactant needs to be protonated for the dye to transfer to the oil phase. Because the pKa of fluorescein is probably about 4.2 similar to that of benzoic acid, it seems more likely that it is the emulsifier that needs to be protonated. Accordingly, the pH of the drilling fluid sample can be adjusted, for example by adding an acid or a base, in order to provide an accurate dye transfer indicative of the concentration of the emulsifier.

The samples in FIGS. 8A-8D and 9A-9E were prepared to evaluate whether dyes having a different pH than the fluorescein dye would have an effect on dye transfer. To further understand the pH effect on dye transfer, two different dyes were selected which are pH indicators in different pH ranges. One dye for FIGS. 8A-8D was Bromophenol-Blue, whose aqueous solution is yellow at a pH<3 and blue/violet at a pH>4.6. The other dye for FIGS. 9A-9E was Clayton-Yellow, whose aqueous solution changes from yellow to orange across a pH range of 12.2-13.2. For FIGS. 8A-8D, in every vial, 10 g aqueous solution containing 0.0075 wt % Bromophenol-Blue dye in deionized water was mixed with 2 g oil solution of 5 wt % polyamide emulsifier in a blend of cyclic and n-alkanes oil by vigorous shaking—except for FIG. 8A, which did not include the emulsifier. Fluids shown in FIGS. 8B-8D had varying pH that was adjusted using NaOH of the water phase, and increased from left to right as follows: pH 9.95, 10.75, and 11, respectively. For FIGS. 9A-9E, in every vial, 10 g aqueous solution containing 0.0075 wt % Clayton-Yellow dye in deionized water was mixed with 2 g oil solution of 5 wt % polyamide emulsifier in a blend of cyclic and n-alkanes oil by vigorous shaking. Fluids shown in FIGS. 9A-9E had varying pH that was adjusted using NaOH of the water phase, and increased from left to right as follows: pH 8.95, 10.48, 10.79, 11.12, and 11.96, respectively. Similar to fluorescein, these dyes failed to transfer to the oil phase at a pH>~11. These results suggest that the high pH of the water de-protonated the emulsifier that may have a pKa of about 9.5 in water. These results seem to support the theory proffered above regarding fluorescein dye of FIGS. 7A-7E that it is the emulsifier and not the dye that becomes de-protonated due to the pH of the water phase.

Figure 10A:
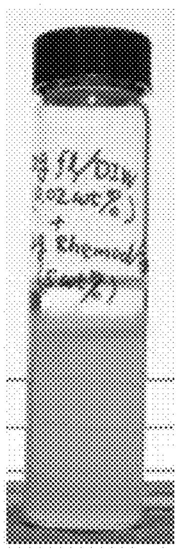
FIGS. 10A and 10B are photographs of an invert emulsion showing potential interference in dye transfer by two different surfactants.
Figure 10B:
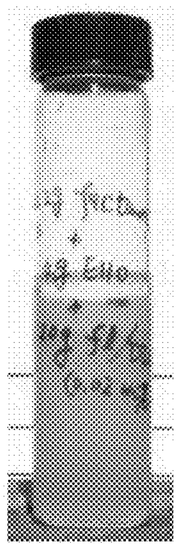

The discovery of dye transfer in the presence of emulsifiers suggests that a simple color test for determining the concentration of free or available emulsifier in oil-based drilling fluids (OBMs) that can be used onsite at the drilling location. However, for the test to be accurate, other additives in the drilling fluid should not interfere with the dye transfer from the water phase to the oil phase. Other surfactant-like additives that are sometimes used in OBMs are TOFA, RHEMOD L™ viscosifier of a modified fatty acid, and FACTANT™ emulsifier of a highly concentrated tall oil derivative. As discussed above and shown in FIG. 6A, TOFA cannot transfer dyes from the water phase to the oil phase. In each vial, 20 g of an aqueous solution containing 0.02 wt % fluorescein dye in deionized water was mixed with 4 g of a blend of cyclic and n-alkanes oil and 5 wt % RHEMOD L™ (FIG. 10A) and 5 wt % FACTANT™ (FIG. 10B) by vigorous shaking by hand. As can be seen, both RHEMOD L™ and FACTANT™ failed to transfer dyes from the water phase to the oil phase. Therefore, the color test of emulsifiers based on the dye-transfer phenomenon is not interfered by these surfactant-like components in OBMs, which indicates that an accurate estimation of the concentration of emulsifier can be made.

Figures 11A, 11B, 11C, 11D, 11E, 11F, 11G:
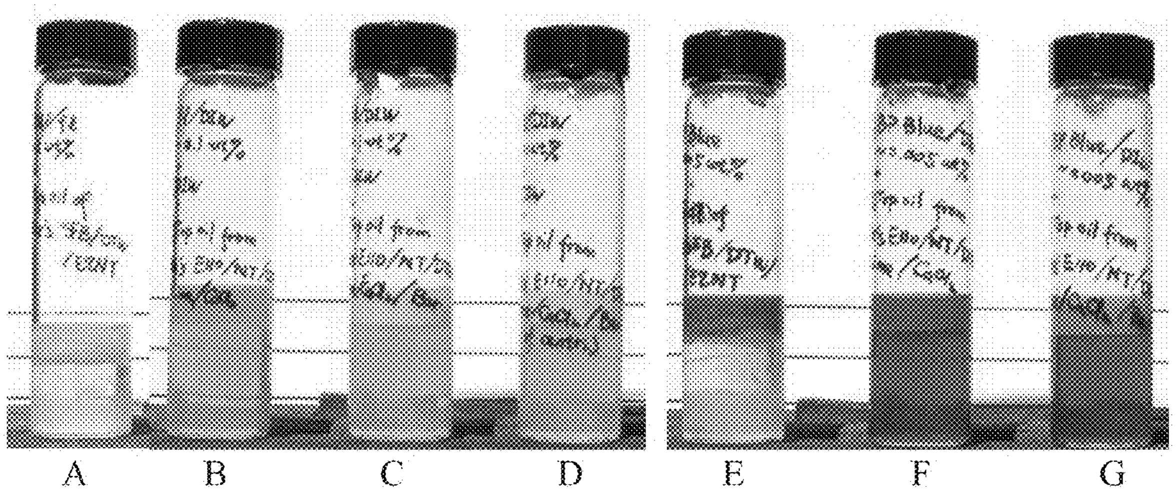
FIGS. 11A-11G are photographs of invert emulsions using top oil from a model drilling mud system with varying ingredients and fluorescein dye or bromophenol-blue dye.

For FIGS. 11A-11G, testing was performed on a series of model mud systems. The model mud systems simulate drilling muds used on well sites. The components and amount are listed below in Table 1. A polyamide emulsifier and a blend of cyclic and n-alkanes oil as the base oil was used. Fluorescein dye was used for FIGS. 11A-11D, and Bromophenol Blue was used for FIGS. 11E-11G. The top oil in FIG. 11D was centrifuged to remove possible water and lime suspended in the model mud. As shown, with the same amount of dye added in the water phase, the top oil of a simple emulsion without any lime or $CaCl_2$) took almost all of the dye molecules from the water phase to the oil phase (FIGS. 11A and 11E). For the systems with lime and $CaCl_2$), however, the top oil only transferred a small portion of dye molecules (FIGS. 11B and 11F). Further, with the addition of barite, most of dye molecules were left in the water phase (FIGS. 11C, 11D, and 11G). The results suggested two possibilities. The first is that there was not enough free emulsifier left in the top oil for the systems with lime, $CaCl_2$), and barite. The second is that lime and $CaCl_2$) modified the emulsifier molecules making them lose the capability of transferring dye molecules.

TABLE 1

| Ingredient (g) | FIG. 11A | FIG. 11B | FIG. 11C | FIG. 11D | FIG. 11E | FIG. 11F | FIG. 11G |
|---|---|---|---|---|---|---|---|
| Base oil | 40 | 40 | 40 | 40 | 40 | 40 | 40 |
| Emulsifier | 2 | 2 | 2 | 2 | 2 | 2 | 2 |
| Water | 20 | 20 | 20 | 20 | 20 | 20 | 20 |
| Lime | 0 | 0.2 | 0.2 | 0.2 | 0 | 0.2 | 0.2 |
| $CaCl_2$ | 0 | 8 | 8 | 8 | 0 | 8 | 8 |
| Barite | 0 | 0 | 10 | 10 | 0 | 0 | 10 |
| Centrifuge | N | N | N | Y | N | N | N |

Figure 12A:
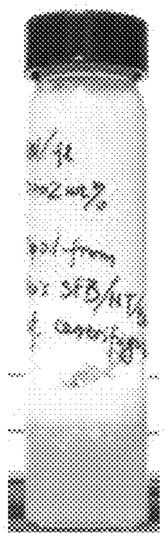
FIGS. 12A and 12B are photographs of an invert emulsion with and without calcium chloride to determine the effect of salt on dye transfer.
Figure 12B:
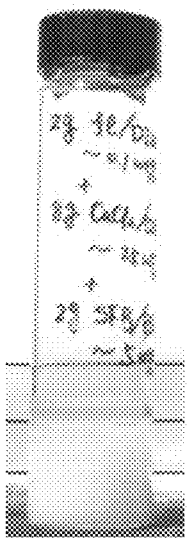

In order to determine which of the two possibilities was true, further evaluation was performed. DLS measurements in FIGS. 5A and 5B showed that there were plenty of emulsifier micelles formed; however, the centrifuged top oil sample failed in the dye-transfer test as shown in FIG. 11D. When the dye concentration from FIGS. 11A-11D was reduced by 10 times to 0.002 wt % as shown in FIG. 12A, all of the dye remained in the water phase. This result suggests that it was the lime and $CaCl_2$) that disturbed the dye transfer capability of the emulsifier. Further, to separate whether it was the $Ca^{2+}$ or the $Ca(OH)_2$, a sample was prepared in which 20 wt % $CaCl_2$) was added in the water phase (FIG. 12B). As can be seen, the dye transferred from the water phase to the oil phase in FIG. 12B that contained a high concentration of calcium ions. Therefore, it is theorized that it was the lime that modified the emulsifier leading to the reduction/loss of its dye-transfer capability, which is similar to the effect of NaOH as discussed in relation to FIGS. 7A-7E.

Figures 13A, 13B, 13C, 13D, 13E, 13F, 13G, 13H, 13I, 13J:
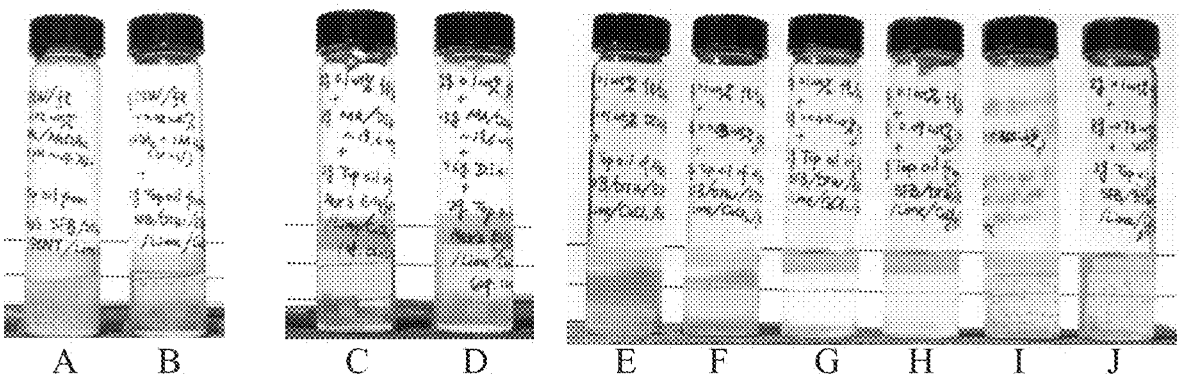
FIGS. 13A-13J are photographs of invert emulsions to evaluate the effect of acids or acidic buffers on fluorescein dye transfer.
Figures 14A, 14B, 14C, 14D:
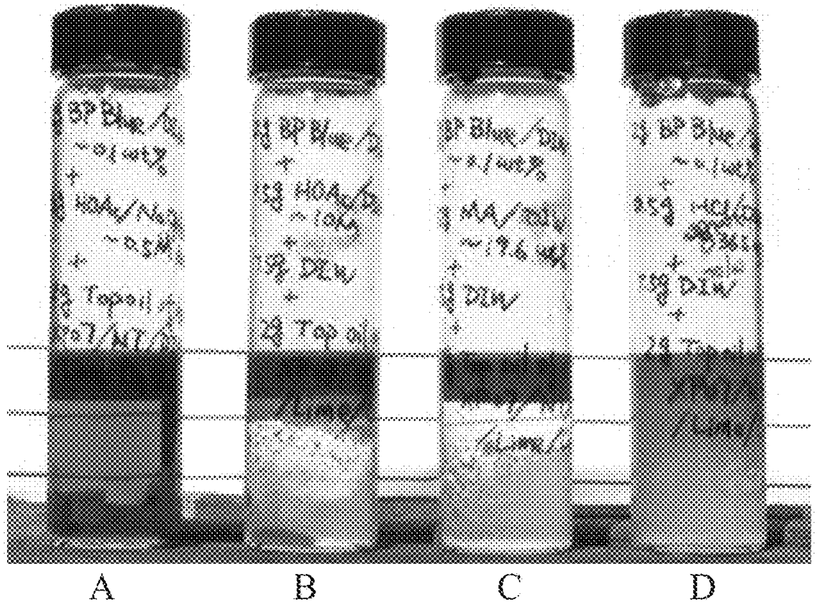
FIGS. 14A-14D are photographs of invert emulsions to evaluate the effect of acids or acidic buffers on bromophenol-blue dye transfer.

To try and recover the dye-transfer ability of the emulsifiers in these systems, samples with acidic buffers or acids added to the water phase were tested. The acidic buffers and acids that were tested included equal moles of acetic acid and sodium acetate, acetic acid, maleic anhydride, and hydrochloric acid (HCl) (FIG. 13 with fluorescein dye and FIG. 14 with Bromophenol Blue). For FIGS. 13A-13K, every vial contained 10 g of an aqueous solution of 0.02 wt % fluorescein and deionized water mixed with 2 g top oil of the model mud system (oil/emulsifier/water/lime/$CaCl_2$)/Barite) by vigorous shaking with the following: an acidic buffer made of equal moles of acetic acid and sodium acetate (PH ~4.75) at a concentration of acetic acid and sodium acetate 0.1875 wt % (FIG. 13A) and 1.875 wt % (FIG. 13B); maleic anhydride at a concentration of 15.6 wt % (FIG. 13C) and 0.98 wt % (FIG. 13D); and HCl at a concentration of 0.008 wt % (FIG. 13E), 0.018 wt % (FIG. 13F), 0.037 wt % (FIG. 13G), 0.072 wt % (FIG. 13H), 0.292 wt % (FIG. 13I), and 0.584 wt % (FIG. 13J). For FIGS. 14A-14D, every vial contained 10 g of an aqueous solution of 0.02 wt % Bromophenol Blue and deionized water mixed with 2 g top oil of the model mud system (oil/emulsifier/water/lime/$CaCl_2$)/Barite) by vigorous shaking with the following: an acidic buffer made of equal moles of acetic acid and sodium acetate (PH ~4.75) at a concentration of acetic acid and sodium acetate 2.33 wt % (FIG. 14A); acetic acid at a concentration of 1.874 wt % (FIG. 14B); maleic acid at a concentration of 0.98 wt % (FIG. 14C); and HCl at a concentration of 0.018 wt % (FIG. 14D).

It can be seen that, for samples having either the equal moles of acetic acid and sodium acetate or the maleic anhydride, fluorescein-transfer only partially recovered (FIGS. 13A-13D). HCl showed dye transfer could be mostly recovered, but the HCl had to be in a sufficient concentration (FIG. 13G, 0.037 wt % HCl in the water phase), which may not be a viable option for practical applications due to the strong acid nature of HCl and due to the dependence of recovery on the amount of HCl. For Bromophenol-Blue, however, although the blend of equal moles acetic acid and sodium acetate only partially recovered the dye-transfer ability of the emulsifier (FIG. 14A), both acetic acid and maleic anhydride (FIGS. 14B and 14C, respectively) can fully recover the emulsifier. Because acetic acid is safer than maleic anhydride, an aqueous solution of Bromophenol-Blue and acetic acid seemed to be a good choice in the color test of emulsifiers. This indicates that the specific dye used, and the specific acid or buffer can be selected such that the dye-transfer capabilities are achieved.

Figure 15:
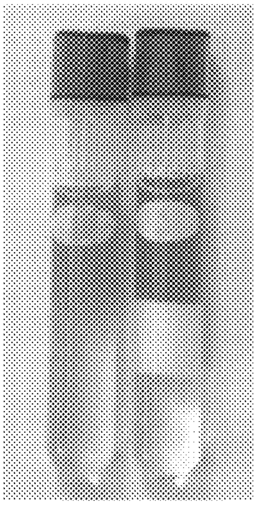
FIG. 15 are photographs of invert emulsions using top oil from a field mud with and without an emulsifier.

With reference to FIG. 15, to check the applicability of the color test in the field, the top oil of an ester and olefin-based field mud (13.9 lb/gal) sampled at a Galveston, Texas, USA wellsite was added into some fluorescein dye water, shaken, and let stand, without and with a polyamide emulsifier. As shown in FIG. 15, the water phase remained colored when no emulsifier was added into the top oil (left tube) and turned colorless with the addition of the emulsifier (right tube), giving an obvious color change, and indicating that when free or available emulsifier is added, the test is applicable for use in the field.

Figures 16A, 16B, 16C:
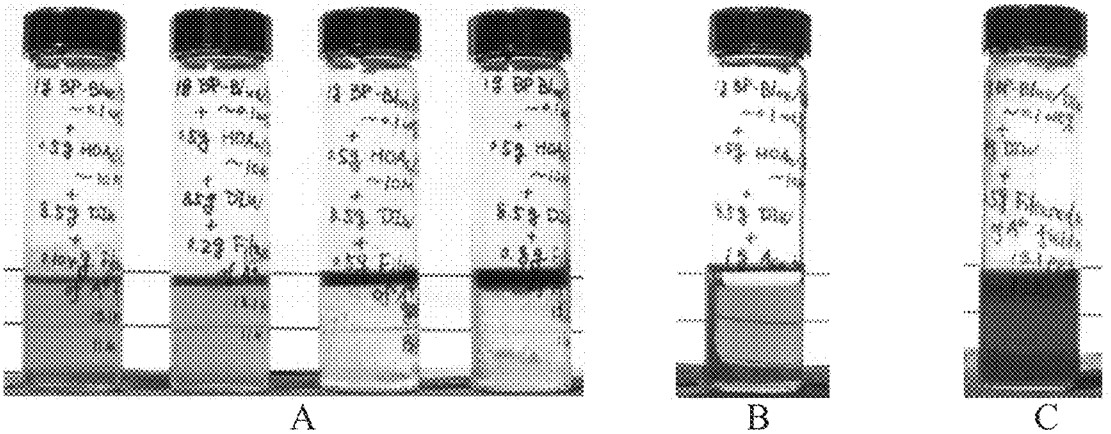
FIGS. 16A-16C are photographs of invert emulsions using top oil from a field mud with and without an acid to determine the effect of lime on dye transfer.
Figures 17A, 17B, 17C, 17D:
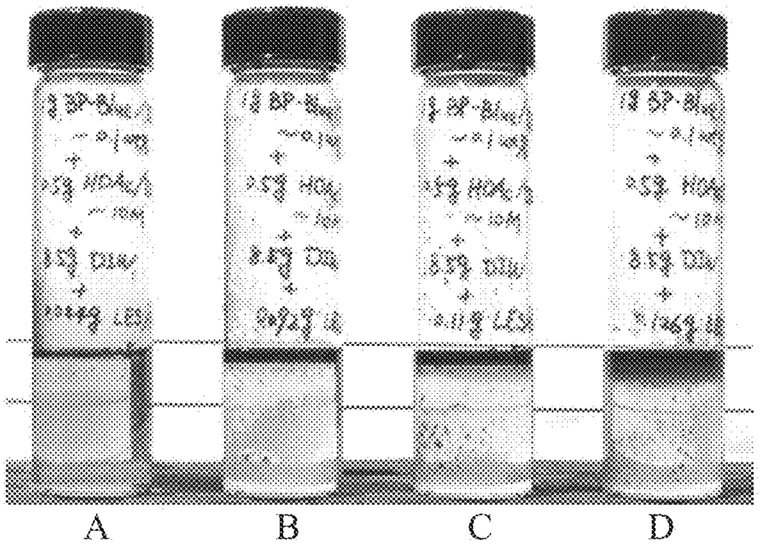
FIGS. 17A-17D are photographs of invert emulsions using top oil from a field mud with an acid and varying concentrations of an emulsifier.

Further testing was performed to evaluate use in the ester and olefin-based field mud sample. In FIG. 16A, 10 g aqueous solution of 0.01 wt % Bromophenol-Blue and deionized water was mixed with increasing amounts from left to right (0.104 g, 0.2 g, 0.5 g, and 0.8 g, respectively) of top oil from the field mud without any emulsifier. Acetic acid at a concentration of 1.875 wt % was used as a buffer acid. The top oil was filtered through filter paper (2.7 μm pores) before use. For comparison, another sample containing 1 g top oil was prepared as shown in FIG. 16B. Another sample except without the acetic acid as FIG. 16A with 0.5 g of top oil was prepared as shown in FIG. 16C. The study on the NaOH systems and on the model mud systems showed that the emulsifiers lost their dye-transfer ability when NaOH was present in the water phase, or when the emulsifiers had been in contact with aqueous solutions with lime present. Therefore, the failure of the top oil to extract dye from the water phase (the sample in the left tube in FIG. 15), presented two possibilities. One is that there was not enough emulsifier in the top oil; and the other is that the emulsifier in the top oil lost their dye-transfer ability due to the lime in the field mud. The results shown in FIGS. 16A and 16B, where acetic acid (1.875 wt %) was added into each sample, suggested it might be the second possibility. By comparing FIG. 16A with FIG. 16C, it can be seen that the addition of a small amount of acetic acid (1.875 wt %) into the water phase recovered the dye-transfer ability of the top oil of the ester and olefin-based field mud. In FIG. 16, the top oil was filtered through the piece of filter paper before use in order to make the results more comparable to those of filtered oil of the same field mud. No obvious difference was seen between samples containing un-filtered top oil and samples containing filtered top oil. From FIG. 16A, it can be seen that increasing amounts of dye was transferred to the top oil when the amount of the top oil in each sample was increased (from 0.104 g to 0.8 g). At the value of 0.8 g. almost all the dye molecules were extracted to the oil phase. Therefore, if the amount of an emulsifier/oil solution (e.g., 0.8 g) with a known concentration of emulsifier needed to extract all of the dye from the water phase under exactly the same conditions can be predetermined, then the emulsifier concentration can be estimated in the top oil of a field mud on the well site. This can be accomplished by adding the same amount, for example 0.8 g of the top oil of the field mud to the aqueous solution with the dye and visually inspecting the amount of dye that is transferred.

Dye test of a solution with a different polyamide emulsifier at 5 wt % and a blend of cyclic and n-alkanes base oil were prepared for FIGS. 17A-17D. 10 g aqueous solution of 0.01 wt % Bromophenol-Blue and deionized water and acetic acid 1.875 wt % as a buffer acid were mixed with increasing amounts 0.044 g, 0.092 g. 0.11 g, and 0.126 g. FIGS. 17A-D, respectively of the emulsifier/oil. Comparing FIG. 16A and FIG. 17, we can see that the dye-transfer capability of the 0.8 g top oil of the field mud is about the same as that of the 0.126 g base oil with 5 wt % polyamide emulsifier. Previous experiments suggested that it was the amount of the emulsifier that decides the dye-transfer capability. Therefore, because the amount of dye that was transferred was about the same, the 0.8 g top oil should contain 0.126 g×5 wt %=0.0063 g emulsifier. This means that the concentration of the emulsifier in the top oil is 0.0063/0.8=0.8 wt %. This shows that it is possible to quantify the amount of emulsifier in a field mud sample by comparing the amount of dye that was transferred in the test sample to that of a reference sample with a known concentration of emulsifier.

In conclusion, from the experiments it appears that transfer of fluorescein or other dyes from a water phase to an oil phase can be used as an indication of the amount of free emulsifier in the oil phase of a drilling fluid. The dye is solubilized into invert micelles in the oil phase, though it appears this is prevented at a pH greater than 10.5 or 11 depending on the specific dye used. It is theorized this may be due to de-protonation of the emulsifier in the oil phase. Accordingly, any excess alkali ingredients in the drilling fluid must be neutralized for the transfer to occur. There has been a difference found between filtered field mud oil and top oil in the dye test. The filtered oil cannot transfer dye as effectively as the top oil. The reason might be that during filtration most of the free emulsifier in the OBM was trapped onto the other components in the OBM (such as solid particles, water droplets, and/or fluid-loss additives), which blocked the pores in the filter paper resulting in less emulsifier in the filtered oil than in the top oil. Moreover, the experiments showed that it was the amounts of the dye and the active component in the emulsifier loaded into the testing tube that mattered. Therefore, as long as the total mass ratio of the dye versus the emulsifier is set at the value for the emulsifier to extract all of the dye from the aqueous solution, both the amounts of the aqueous and oil solutions and the concentrations of the dye and the emulsifier can be adjusted to suit the practical conditions.

Therefore, the various embodiments are well adapted to attain the ends and advantages mentioned as well as those that are inherent therein. The particular embodiments disclosed above are illustrative only, as the various embodiments may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While compositions, systems, and methods are described in terms of "comprising," "containing," or "including" various components or steps, the compositions, systems, and methods also can "consist essentially of" or "consist of" the various components and steps. It should also be understood that, as used herein, "first," "second," and "third," are assigned arbitrarily and are merely intended to differentiate between two or more test fluids, vials, etc., as the case may be, and do not indicate any sequence. Furthermore, it is to be understood that the mere use of the word "first" does not require that there be any "second," and the mere use of the word "second" does not require that there be any "third," etc.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent(s) or other documents that may be incorporated herein by reference, the definitions that are consistent with this specification should be adopted.

What is claimed is:

1. A method for determining an amount of free emulsifier in a drilling fluid comprising:

obtaining an aliquot of the drilling fluid, wherein the drilling fluid comprises a base oil, an aqueous phase, and an emulsifier;

obtaining top oil from the aliquot;

preparing an aqueous solution comprising water and a dye at a concentration by weight percent of the water;

placing an amount of the top oil and an amount of the aqueous solution into a testing vial;

evaluating an amount of the dye transferred from the aqueous solution phase to the top oil phase in the testing vial;

correlating the amount of the dye transferred from the aqueous solution phase to the top oil phase to the concentration of free emulsifier in the drilling fluid; and determining the amount of free emulsifier in the drilling fluid based on the amount of the dye transferred from the aqueous solution phase to the top oil phase.

2. The method according to claim 1, further comprising: mixing the top oil and the aqueous solution in the testing vial after the top oil and the aqueous solution have been placed in the testing vial; and allowing the testing vial to remain stationary to allow any of the free emulsifier in the top oil to transport the dye from the aqueous solution to the top oil.

3. The method according to claim 1, wherein the emulsifier is a polyamide emulsifier.

4. The method according to claim 1, wherein the emulsifier has a hydrophilic/lipophilic balance greater than 3.

5. The method according to claim 1, wherein the water is selected from deionized water, fresh water, or water containing a water-soluble salt.

6. The method according to claim 1, wherein the dye is a water-soluble dye selected from fluorescein, Brilliant-Yellow, Bromocresol-Green, sodium 1,2-naphthoquinone-4-sulfonate, Thymol-Blue, Bromophenol Blue, or Clayton-Yellow.

7. The method according to claim 1, wherein the dye is in a concentration in a range of 0.1 to 5 wt % of the water.

8. The method according to claim 1, wherein the amount of top oil from the aliquot placed in the testing vial is in a range from 0.5 to 10 grams.

9. The method according to claim 1, wherein the amount of the aqueous solution is greater than the amount of the top oil.

10. The method according to claim 1, wherein the top oil is obtained from the aliquot by allowing the aliquot to settle within a collections container and withdrawing the top oil that has floated to the top of the container; centrifuging the aliquot to separate the top oil from the aqueous phase; or filtering the aliquot through a filter paper into a container and then collecting the top oil from the container.

11. The method according to claim 10, wherein the top oil is obtained by filtering the aliquot through the filter paper, and wherein the filter paper has a pore size in a range of 2 micrometers to 20 millimeters.

12. The method according to claim 1, wherein the aqueous solution further comprises a pH adjuster, an acid, or an acidic buffer.

13. The method according to claim 12, wherein the aqueous solution has a pH in a range of 5 to 11.

14. The method according to claim 1, further comprising preparing a reference sample by placing an amount of the base oil of the drilling fluid with a known concentration of the emulsifier and an amount of an aqueous solution comprising water and the dye at a concentration by weight percent of the water into a reference sample vial.

15. The method according to claim 14, wherein determining the amount of free emulsifier in the drilling fluid comprises visually comparing the amount of the dye transferred from the aqueous solution phase to the top oil phase in the testing vial against an amount of dye transferred from the aqueous solution phase to the base oil phase in the reference sample vial.

16. The method according to claim 15, wherein determining the amount of free emulsifier in the drilling fluid further comprises adding incremental amounts of the emulsifier in the drilling fluid to the testing vial until a desired amount of the dye is transferred to the top oil phase while visually comparing against the amount of dye transferred in the reference sample vial.

17. The method according to claim 14, wherein determining the amount of free emulsifier in the drilling fluid comprises:

measuring an absorbance of the dye transferred to the top oil in the testing vial;

measuring an absorbance of the dye transferred to the base oil in the reference sample vial; and comparing the absorbance from the testing vial against the absorbance from the reference sample vial.

18. The method according to claim 17, wherein determining the amount of free emulsifier in the drilling fluid further comprises:

preparing more than one reference sample, wherein each of the reference samples are identical except for a different concentration of the emulsifier;

generating a calibration curve from an absorbance from each of the reference samples; and comparing the absorbance from the testing vial to the calibration curve.

* * * * *